United States Patent [19]

Inada et al.

[11] Patent Number: 5,124,250
[45] Date of Patent: Jun. 23, 1992

[54] ELEMENT FOR ASSAYING RHEUMATOID FACTOR QUANTITATIVELY AND METHOD OF ASSAYING THE SAME

[75] Inventors: Mami Inada; Hakuji Matsumoto, both of Ohtsu; Tsuneo Hanyu, Tsuruga; Kyoichi Kano, Tokyo, all of Japan

[73] Assignee: Toyo Boseki Kabushiki Kaisha, Osaka, Japan

[21] Appl. No.: 415,237

[22] PCT Filed: Jan. 11, 1989

[86] PCT No.: PCT/JP89/00024
§ 371 Date: Sep. 11, 1989
§ 102(e) Date: Sep. 11, 1989

[87] PCT Pub. No.: WO89/06800
PCT Pub. Date: Jul. 27, 1989

[30] Foreign Application Priority Data
Jan. 12, 1988 [JP] Japan .................................. 1-5546

[51] Int. Cl.⁵ ............... G01N 33/53; G01N 33/547; G01N 33/564
[52] U.S. Cl. .................. 435/7.9; 435/7.92; 435/7.94; 435/970; 436/513; 436/532; 436/509; 436/811; 422/57
[58] Field of Search ............ 435/7.9, 7.2, 7.94; 436/518, 509, 528, 513, 531, 532, 509, 807, 809, 810; 422/68.1; 424/487; 530/387

[56] References Cited
U.S. PATENT DOCUMENTS
4,020,151  4/1977  Bolz et al. .
4,792,527  12/1988  Uchida et al. ............ 436/533

FOREIGN PATENT DOCUMENTS
000026  1/1980  PCT Int'l Appl. .

OTHER PUBLICATIONS
P. Tijssen, "Chapter 13 The Immobilization of Immunoreactants on Solid Phases", Practice and Theory of Enzyme Immunoassays. pp. 297–314 (1985).
Journal of Immunological Methods, vol. 71 (1984), Ingvar Teitsson et al., [Use of Monoclonal Antibodies and F(ab')₂ Enzyme Conjugates in ELISA for IgM, IgA and IgG Rheumatoid Factors] pp. 149–161.
Acta path. microbiol. immunol. scand. Sect. C, vol. 95, No. 4, (1987), Kjetil Asbakk et al., [Rheumatoid Factors in Psioratic Scale, Serum and Circulating Immune Complexes Detected by An Isotype-Specific elisa] pp. 161–166.

Primary Examiner—Esther L. Kepplinger
Assistant Examiner—Carol E. Bidwell
Attorney, Agent, or Firm—Wegner, Cantor, Mueller & Player

[57] ABSTRACT

An element for assaying a rheumatoid factor quantitatively in biosamples, comprising a polyalkyl methacrylate solid carrier and serum albumin immobilized thereon, the serum albumin being immunologically bound with anti-albumin rabbit IgG, and a method of assaying a rheumatoid factor quantitatively by immunoglobulin class in which the element is reacted with the biosample, then the element-bound rheumatoid factor is reacted with enzyme-labeled anti-human IgG, enzyme-labeled anti-human IgM or enzyme-labeled anti-human IgA, and then the amount of the marker enzyme is determined.

2 Claims, No Drawings

ELEMENT FOR ASSAYING RHEUMATOID FACTOR QUANTITATIVELY AND METHOD OF ASSAYING THE SAME

FIELD OF THE INVENTION

The present invention relates to an element for assaying a rheumatoid factor quantitatively in biosamples such as of human serum by immunoglobulin class, and to a method for assaying the same.

BACKGROUND OF THE INVENTION

Rheumatoid factor (RF) is known to appear highly frequently in serum and synovial fluid of patients suffering from chronic articular rheumatism, one of the autoimmune diseases. It is also known that patients test positive for rheumatoid factor in collagen diseases, liver diseases, infectious diseases and other diseases as well. Assay for a rheumatoid factor is very useful in diagnosing and treating these diseases including chronic articular rheumatism.

Rheumatoid factor is considered an antibody formed by misrecognition of immunoglobulin. This is suggested, for example, by the fact that an immune complex comprising IgG and rheumatoid factor is formed in synovial fluid of chronic articular rheumatism patients. Traditionally, rheumatoid factor has been identified as a macroprotein with a molecular weight of about 1,000,000 belonging mainly to the IgM class. It has recently been confirmed, however, that there are other types of rheumatoid factor, belonging to the IgG class and IgA class. Assay for a rheumatoid factor by immunoglobulin class is expected to permit efficient elucidation of disease cause and efficient diagnosis.

The widely used assay methods are the RA assay method which utilizes latex agglutination and the RAHA assay method which utilizes passive hemoagglutination of sheep red blood cell. Although semi-quantitative determination by serial dilution is also available in these assay methods, all these methods are based on nothing more than qualitative reaction. Therefore, these assay methods give rise to difficulty, for example, in accurate determination of time-related changes in rheumatoid factor.

Some quantitative assay methods for a rheumatoid factor have been developed as improvement of these qualitative or semi-quantitative methods. Examples of the quantitative assay method for a rheumatoid factor include the laser nephelometric method, the turbidimetric immunoassay method and the labeling immunoassay method. Among these quantitative assay methods, neither the laser nephelometric method nor the turbidimetric immunoassay method permits accurate assay of rheumatoid factor of, for example, the IgG class, though they both permit assay of high molecular rheumatoid factor of the IgM class alone since they are based on agglutination. On the other hand, the labeling immunoassay method permits assay of rheumatoid factor by immunoglobulin class since it utilizes the high specificity and high detection sensitivity of antigen-antibody reaction wherein antigen or antibody is immobilized to an insoluble carrier. For example, the following method is described by Teitsson, I. and H. Valdimarsson in the Journal of Immunological Methods, 71, 149 (1984). First, an element is prepared which comprises an insoluble carrier such as polystyrene and immunoglobulin such as rabbit IgG or denatured human IgG coupled thereon. To this element is added a sample containing rheumatoid factor, and this is followed by rheumatoid factor binding to IgG in the element. The IgG-bound rheumatoid factor thus obtained is then reacted with each of labeled antibodies such as labeled anti-human IgG, labeled anti-human IgM and labeled anti-human IgA. The amount of each labeled antibody bound to the rheumatoid factor is then measured. This determination method permits assay of rheumatoid factor in the sample by immunoglobulin class (e.g. IgG-class RF, IgM-class RF or IgA-class RF). However, this method has a drawback that the immunoreactivity of carrier-coupled IgG decreases noticeably during storage in cases where the above-mentioned element comprising an insoluble carrier and IgG coupled thereto is prepared and stored in a dry state before use.

Since assay of rheumatoid factor by immunoglobulin class is very useful in etiologic elucidation, diagnosis and treatment of various diseases related to rheumatoid factor, it is expected that an assay element and a method will be developed which permit assay of rheumatoid factor with high reproducibility and high precision.

DETAILED DESCRIPTION OF THE INVENTION

The above-mentioned drawback in prior art is overcome by the present invention. Accordingly, an object of the present invention is to provide an element for assaying a rheumatoid factor quantitatively which permits assay of rheumatoid factor by immunoglobulin class with high reproducibility and high precision on the basis of the labeling immunoassay method and which has excellent long-term storage property, and an assay method using this element.

The element for assaying a rheumatoid factor quantitatively of the present invention is characterized by a polyalkyl methacrylate solid carrier carrying on the surface thereof albumin produced from blood, said albumin being immunologically bound with anti-albumin rabbit IgG.

The assay method for rheumatoid factor of the present invention is characterized by reacting an unknown amount of rheumatoid factor in a biosample with an element for assaying a rheumatoid factor comprising a polyalkyl methacrylate solid carrier carrying on the surface thereof albumin produced from blood, said albumin being immunologically bound with anti-albumin rabbit IgG, reacting the element-bound rheumatoid factor with enzyme-labeled anti-human IgG, enzyme-labeled anti-human IgM or enzyme-labeled anti-human IgA, determining the amount of the marker enzyme bound or not bound to the element and assaying quantitatively IgG-class rheumatoid factor, IgM-class rheumatoid factor or IgA-class rheumatoid factor in the biosample by immunoglobulin class.

The solid carrier used for the element for assaying a rheumatoid factor quantitatively of the present invention is a molding product formed with polyalkyl methacrylate, preferably polymethyl methacrylate, e.g. microplate, bead or tube. The use of this polyalkyl methacrylate carrier reduces nonspecific adsorption in comparison with the use of a solid carrier of another material such as polystyrene or polyamide for assay, thus permitting more accurate assay of rheumatoid factor with high sensitivity.

The element for assaying a rheumatoid factor of the present invention is, for example, prepared as follows: First, albumin produced from blood such as bovine serum albumin (BSA) is dissolved in an appropriate buffer solution and brought into contact with the above-mentioned solid carrier to adsorb and immobilize the albumin produced from blood. After removal of the unadsorbed albumin, a solution of anti-albumin IgG is brought into contact with the carrier to bind the anti-albumin IgG to the carrier-coupled albumin and form an immune complex. After removal of the unbound anti-albumin IgG, a buffer solution containing sugar, for instance, is brought into contact with the immune complex to block the nonspecific binding site on the carrier's surface. After removal of the above buffer solution, the carrier is thoroughly dried using a vacuum drier as needed, whereby the element for assaying a rheumatoid factor quantitatively of the present invention is obtained. An immune complex of albumin and anti-albumin rabbit IgG may be immobilized on the solid carrier by a chemical or physical means. It is desirable that the element for assaying a rheumatoid factor quantitatively thus prepared, together with a desiccant such as silica gel, be sealed in a container filled with nitrogen gas and stored under refrigerating conditions.

As an example of the albumin produced from blood used for the above-mentioned element, mention may be made of bovine serum albumin (BSA). Anti-bovine serum albumin rabbit IgG antibody (α-BSA rab. IgG) is the especially suitable anti-albumin IgG. The use of these components provides an element for assaying a rheumatoid factor with much higher reproducibility in comparison with the use of conventional rabbit IgG or denatured human IgG and which is free of possibility of activity degradation.

When using the above-mentioned element for assaying a rheumatoid factor, rheumatoid factor can be assayed as follows. For example, a biosample such as of human serum is brought into contact with and thoroughly reacted with the element for assaying a rheumatoid factor prepared as above. The rheumatoid factor in the biosample reacts with the albumin-anti-albumin IgG immune complex on the solid carrier. After completion of the reaction, the unreacted substances are removed, and this is followed by reaction with an enzyme-labeled antibody corresponding to the immunoglobulin class of the rheumatoid factor to be assayed (e.g. labeled anti-human IgG, when IgG-class RF is to be assayed). After separation of the labeled antibody which reacted to the rheumatoid factor on the solid carrier and the unreacted labeled antibody, determination is made of the amount of enzyme in the labeled antibody bound with rheumatoid factor or the amount of enzyme in the unbound labeled antibody. The amount of marker enzyme bound to the element for assaying a rheumatoid factor of the present invention is in proportion to the amount of rheumatoid factor present in the biosample, while the amount of marker enzyme not bound to the element is in reverse proportion to the amount of rheumatoid factor in the biosample. Examples of the enzyme used for antibody labeling in the above-mentioned method include peroxidase. Measurement of the marker enzyme is achieved in accordance with an ordinary method. Peroxidase is, for example, measured by coloring reaction using hydrogen peroxide and o-phenylenediamine dihydrochloride. Rheumatoid factor is quantified by immunoglobulin class with high precision by determining the amount of enzyme in the labeled antibody as described above.

The present invention is hereinafter described in more detail by means of the following working examples and comparative example.

EXAMPLE 1

(A) Preparation of element for assaying a rheumatoid factor: To a polymethyl methacrylate microplate was dispensed a 1/15 M phosphate buffered saline (hereinafter abbreviated as PBS, pH 7.2) containing 0.2% BSA at 50 μl per well. After the microplate was kept standing at 4° C. for three days to adsorb BSA, each well was washed twice with 0.01 M PBS (pH 7.2) to remove the unadsorbed substances. To each microplate well was dispensed 50 μl of a solution obtained by diluting 6.0 mg/ml α-BSA rab. IgG (produced by Cappel Co.) with 1/15 M PBS (pH 7.2) at a dilution rate of 400 folds. The microplate was kept standing at 4° C. overnight to form an immune complex by reaction between BSA immobilized on the inside wall of the microplate and α-BSA rab. IgG. After completion of the reaction, each well was washed twice with 0.01 M PBS (pH 7.2). To each well was dispensed 100 μl of 1/15 M PBS (pH 7.2) containing 5% sucrose; the microplate was then kept standing at room temperature for 1 hour for blocking. Finally, each well was washed once with 0.01 M PBS (pH 7.2); the microplate was thoroughly dried using a vacuum drier; the microplate, together with silica gel, was then placed in an aluminum-coated bag, which was then sealed after air replacement with nitrogen gas. This microplate, in the sealed bag, was stored at 4° C. before use.

(B) Assay of rheumatoid factor: To each well of the microplate obtained in (A) above was dispensed 50 μl of serum diluted 101-fold with 0.05 M PBS (pH 7.2) containing 0.5% BSA; this microplate was kept standing at room temperature for 1 hour to carry out reaction. After completion of the reaction, this microplate was washed five times with 0.01 M PBS (pH 7.2) to remove the unreacted substances. A peroxidase-labeled antibody diluted at an appropriate concentration, which corresponds to the immunoglobulin class of the rheumatoid factor to be assayed (e.g. peroxidase-labeled anti-human IgG, when IgG-class RF is to be measured) was then dispensed to the microplate at 50 μl per well. This microplate was kept standing at room temperature for 1 hour to carry out the reaction. After completion of the reaction, this microplate was again washed five times with 0.01 M PBS (pH 7.2) to remove the unreacted substances. To each well was dispensed 50 μl of an o-phenylenediamine dihydrochloride solution (3 mg/ml) containing 0.02% hydrogen peroxide. After 30 minutes of reaction at room temperature, 100 μl of 1 N $H_2SO_4$ was added to each well to terminate the enzyme reaction. The reaction mixture was assayed using a spectrometer for microplates (Microplate EL 310, produced by Biotech Co.) at a wavelength of 490 nm.

(C) Storage stability test: The microplate obtained in (A) above was stored at a controlled temperature of 9° C. ±1° C. and assayed every three months. The samples used were two samples of serum positive for rheumatoid factor (Standards 1 and 2), one sample of serum negative for rheumatoid factor (NHS) and one sample containing no serum (blank). The results are summarized in Table 1(a).

COMPARATIVE EXAMPLE 1

The same polymethyl methacrylate microplate as in Example 1 was used as the solid carrier. To each well of this microplate was dispensed 100 μl of a 20 μg/ml solution of rabbit IgG (produced by Miles Co.), denatured by heating at 56° C. for 30 minutes, in 0.01 M PBS (pH 7.2). This microplate was kept standing at 4° C. overnight. Each well was then washed twice with 0.01 M PBS (pH 7.2). To each well was dispensed 200 μl of 0.01 M PBS (pH 7.2) containing 1% BSA and 5% sucrose. The microplate was kept standing at room temperature for 1 hour for blocking. Finally, the microplate was washed once with 0.01 M PBS (pH 7.2), after which it was dried and stored in the same manner as in Example 1.

The microplate prepared as above was subjected to the same storage stability test as in Example 1. The results are shown in Table 1(b).

TABLE 1(a)

| RF by immuno-globulin class | Sample | Storage period | | |
|---|---|---|---|---|
| | | Start | 3 months | 6 months |
| IgG-RF | Standard 1 | 1.368 | 1.414 | 1.376 |
| | Standard 2 | 0.740 | 0.786 | 0.748 |
| | Blank | 0.116 | 0.107 | 0.108 |
| | NHS | 0.189 | 0.180 | 0.178 |
| IgM-RF | Standard 1 | 0.879 | 0.898 | 0.859 |
| | Standard 2 | 0.273 | 0.252 | 0.275 |
| | Blank | 0.005 | 0.002 | 0.020 |
| | NHS | 0.030 | 0.048 | 0.049 |
| IgA-RF | Standard 1 | 0.670 | 0.821 | 0.674 |
| | Standard 2 | 0.181 | 0.241 | 0.215 |
| | Blank | 0.021 | 0.022 | 0.027 |
| | NHS | 0.019 | 0.028 | 0.025 |

TABLE 1(b)

| RF by immuno-globulin class | Sample | Storage period | | |
|---|---|---|---|---|
| | | Start | 3 months | 6 months |
| IgG-RF | Standard 1 | 1.215 | 1.373 | 1.410 |
| | Standard 2 | 0.650 | 0.610 | 0.656 |
| | Blank | 0.123 | 0.094 | 0.108 |
| | NHS | 0.214 | 0.168 | 0.182 |
| IgM-RF | Standard 1 | 1.092 | 0.570 | 0.506 |
| | Standard 2 | 0.414 | 0.188 | 0.155 |
| | Blank | 0.032 | 0.047 | 0.052 |
| | NHS | 0.307 | 0.257 | 0.238 |
| IgA-RF | Standard 1 | 1.284 | 0.665 | 0.736 |
| | Standard 2 | 0.342 | 0.255 | 0.180 |
| | Blank | 0.050 | 0.083 | 0.082 |
| | NHS | 0.110 | 0.154 | 0.172 |

As is evident from Tables 1(a) and (b), the use of an element for assaying a rheumatoid factor of the present invention, particularly an element comprising BSA-α-BSA rab. IgG immune complex, ensures noticeable improvement in storage stability, in comparison with the use of rabbit IgG. It is evident that the storage stability has improved particularly noticeably in the quantitative assay systems for IgM-class rheumatoid factor and IgA-class rheumatoid factor of Comparative Example 1.

EXAMPLE 2

The influence of the type of solid carrier material on assay sensitivity has examined using two kinds of microplates made of different materials, that is, a polymethyl methacrylate microplate and a polystyrene microplate. Using these two kinds of microplates, rheumatoid factor assay plates were prepared in the same manner as in Example 1, which were then used to measure IgG-class rheumatoid factor in samples of human serum positive for rheumatoid factor and in those of human serum negative for rheumatoid factor (normal human serum) by the same quantitative assay procedure. The results are shown in Table 2.

TABLE 2

| Polymethyl methacrylate plate | | Polystyrene plate | |
|---|---|---|---|
| RF-positive serum | RF-negative serum | RF-positive serum | RF-negative serum |
| 0.732 | 0.214 | 0.520 | 0.875 |
| 0.700 | 0.210 | 0.543 | 0.747 |
| 0.734 | 0.231 | 0.515 | 0.871 |
| 0.720 | 0.290 | 0.507 | 0.863 |

As is evident from Table 2, in the polymethyl methacrylate element for assaying a rheumatoid factor of the present invention, the OD value of serum positive for rheumatoid factor sufficiently exceeds that of serum negative for rheumatoid factor. While in the polystyrene element for assaying a rheumatoid factor used for comparison, the OD value of serum positive for rheumatoid factor is lower than that of serum negative for rheumatoid factor; this polystyrene element cannot be said to have sufficient sensitivity for quantitative assay of rheumatoid factor in human serum. This finding clearly shows that polymethyl methacrylate used in the element for assaying a rheumatoid factor of the present invention is superior to other materials such as polystyrene in assay sensitivity due to reduced nonspecific adsorption.

The present invention provides an element for assaying a rheumatoid factor quantitatively which permits assay of rheumatoid factor by immunoglobulin class with high reproducibility and high precision. The use of this element permits high-sensitive assay of rheumatoid factor by immunoglobulin class on the basis of enzyme immunoassay. The element of the present invention shows very good stability even after long-term storage.

What is claimed is:

1. An element for assaying a rheumatoid factor in a biosample quantitatively, polymethyl methacrylate solid carrier carrying on the surface thereof albumin produced from blood, said albumin being immunologically bound with anti-albumin rabbit IgG.

2. A method of assaying for a rheumatoid factor in a biosample quantitatively, comprising reacting an unknown amount of rheumatoid factor in the biosample with an element for assaying a rheumatoid factor comprising a polymethyl methacrylate solid carrier carrying on the surface thereof albumin produced from blood, said albumin being immunologically bound with anti-albumin rabbit IgG, reacting the element-bound rheumatoid factor with enzyme-labeled anti-human class specific immunoglobulin, wherein said immunoglobulin is selected from the class consisting of anti-human IgA, anti-human IgG and anti-human IgM, and determining the amount of the marker enzyme bound or not bound to the element.

* * * * *